United States Patent [19]

Hayashi

[11] Patent Number: 4,944,922
[45] Date of Patent: Jul. 31, 1990

[54] QUANTITATIVE DISPENSER FOR A LIQUID

[75] Inventor: Hidechika Hayashi, Kanagawa, Japan

[73] Assignee: Tosoh Corporation, Yamaguchi, Japan

[21] Appl. No.: 338,508

[22] Filed: Apr. 14, 1989

Related U.S. Application Data

[63] Continuation of Ser. No. 880,364, Jun. 30, 1986, abandoned.

[51] Int. Cl.$^5$ .................... G01F 11/00; G01N 1/14
[52] U.S. Cl. .................... 422/100; 422/58; 422/65; 422/107; 422/119; 73/863.02; 73/293; 356/375; 436/53
[58] Field of Search .................... 436/47, 48, 50, 53; 73/290 R, 293, 863.02, 864.24, 865.25; 422/55, 58, 63, 65, 100, 106, 107, 119

[56] References Cited

U.S. PATENT DOCUMENTS

| | | | |
|---|---|---|---|
| 4,160,168 | 7/1979 | Funck | 73/293 |
| 4,247,784 | 1/1981 | Henry | 73/293 |
| 4,326,851 | 4/1982 | Bello et al. | 422/63 |
| 4,341,736 | 7/1982 | Drbal et al. | 422/63 |
| 4,410,020 | 10/1983 | Lorenz | 73/293 |
| 4,451,433 | 5/1984 | Yamashita et al. | 422/63 |
| 4,495,149 | 1/1985 | Iwata et al. | 422/67 |
| 4,558,946 | 12/1985 | Galle et al. | 422/63 |

FOREIGN PATENT DOCUMENTS

| | | |
|---|---|---|
| 0185330 | 6/1986 | European Pat. Off. |
| 871532 | 3/1953 | Fed. Rep. of Germany |
| 499096 | 12/1970 | Fed. Rep. of Germany |
| 3113248 | 10/1982 | Fed. Rep. of Germany |
| 58-143269 | 8/1983 | Japan |

Primary Examiner—David L. Lacey
Assistant Examiner—Lori Johnson
Attorney, Agent, or Firm—Sughrue, Mion, Zinn, Macpeak & Seas

[57] ABSTRACT

A quantitative dispenser for a liquid includes a pipette having a downwardly directed nozzle which serves to pick up and deliver a predetermined quantity of a liquid and a mechanism for moving the pipette downwardly to dip the lower end of the pipette into the liquid supply. A detector is provided for detecting reflection of light which is projected downwardly to the surface of the liquid while the pipette is moved downwardly to approach the surface. A control circuit is connected to the detector to determine the stop point for the downwardly moving pipette with the aid of information received from the detector. The detector is provided with a spot type reflection sensor having a light convergent optical element having a focal point at a certain distance below the detector whereby the stop point of the downwardly moving pipette is determined so as to correspond to a point of maximum intensity of the incoming reflected light.

12 Claims, 7 Drawing Sheets

QUANTITATIVE DISPENSER FOR A LIQUID

This is a continuation of Ser. No. 880,364, filed Jun. 30, 1986, now abandoned.

BACKGROUND OF THE INVENTION

The present invention is directed to a quantitative dispenser for small amounts of liquid samples or reagents and more specifically to a quantitative dispenser using an optical sensing device for controlling the amounts of liquid to be dispensed.

In the fields of biology and medicine, various methods of analysis have been proposed for detecting trace substances in body liquids and, in correlation with the analyses, various systems and devices have been proposed for automatic qualitative and quantitative analyses. One of the common requisites arising in these systems and devices is the strict control of the amount of liquid samples and reagents to be added to the reaction chamber and the prevention of contamination of the samples from each other. For this reason, pipettes, such as those called micropipettes, are usually employed which are manufactured with a high degree of precision and contain a disposable tip. In employing these micropipettes, the disposable tips are disposed of after each sample to avoid contamination of the samples from each other. The sample is usually sucked into the pipette by means of a negative air pressure.

As mentioned above, the strict control of the amount of the liquid samples in reagents is necessary for minimizing variations in the amounts of the samples and for obtaining reliable results, particularly in an immunological estimation. On the other hand, the use of disposable tips is also desirable to avoid contamination of the samples from each other since the concentration ratio of minute components can sometimes reach up to $10^4-10^6$ depending on samples in the immunological measurements of the biological materials. Even when micropipettes having disposable tips are used it is still absolutely essential that the minute amounts of liquid to be dispensed must be determined with a high degree of precision and that controls are necessary for positioning the micropipettes relative to the reservoir from which the liquid samples or reagents are taken. More particularly, if a negative pressure is utilized for taking up the sample solution, the negative pressure can be strictly controlled when the pipette is inserted in a sample vessel. The depth to which the nozzle of the pipette is immersed in the sample solution is likely to vary depending on the size of the sample. The variation may give rise to an error in the quantitative dispensing which cannot be ignored. The same problem also arises when the surface of the sample solution is concave due to the formation of a meniscus or the vessel itself is in a slant position and the diameter of the vessel is small.

In the past it has been proposed to install detectors to sense the level of the liquid surface in a dispensing device. However, an electrode type of detector involves contamination and a non-contact type optical detector in general is not sufficiently precise with tolerances of several millimeters and furthermore cannot accurately operate with turbid solutions or slanted surfaces. In fact an error of several millimeters in immersion may introduce, for example, up to ten percent of dispersion when 5 $\mu$l of solution is taken with a pipette of 200 $\mu$l capacity.

SUMMARY OF THE INVENTION

The present invention provides a new and improved quantitative dispenser for a liquid which is capable of dispensing a precisely controlled amount of liquid when a minute amount of liquid is to be taken up.

The present invention provides a new and improved quantitative dispenser for a liquid which is favorably applicable to an automatic analyser, particularly to the portion of an automatic analyser for estimating immunological reactions.

The quantitative dispenser for a liquid according to the present invention is comprised of a pipette having a downwardly directed nozzle which serves to pick up and deliver a liquid, a mechanism for moving the pipette downwardly to immerse the lower end of the pipette in the liquid and a detector for detecting reflection of light which is projected downwardly to the surface of the liquid while the pipette is being moved downwardly to approach the surface and means for determining the stop point of the downwardly moving pipette with the aid of information from the detector, said detector being provided with a spot type reflection sensor having a light convergent optical element with a focal point at a certain distance below the optical element whereby the stop point of the downwardly moving pipette is determined so as to correspond to a point of maximum intensity of the incoming reflected light.

The mechanism for moving the pipette downwardly may be comprised of a support frame on which the indication device of the pipette is supported for movement in the vertical direction and means for moving the frame up and down such as a pulse motor operating through an intermediate cam mechanism. The spot type reflection sensor to be used in the present invention may be comprised of a light emitting portion and a light receiving portion in which the light from the light source and reflected light are transmitted through a convergent optical element such as a convex lens. The portions may be either assembled in a unitary body or arranged separately in appropriate positions relative to each other. The maximum intensity point of the reflected light detected by the reflection type sensor can be detected by converting the reflected light into an electrical signal and by detecting the high peak of the electrical signal.

When such a sensor is used, the maximum intensity of the incoming reflected light occurs when the surface of the liquid coincides with the focus point of the light irrespective of a slanted surface or the turbidity of the liquid. The stop point of the downwardly moving pipette as determined by the maximum intensity makes it possible to precisely control the depth to which the nozzle of the pipette is immersed in the liquid.

Generally the present invention is favorably applied to those devices for analysis and measurement in which the quantitative dispensing of 1000 $\mu$l or less of a liquid is required. More particularly the dispenser according to the present invention is favorably used in carrying out estimations in immunological and biochemical reactions where a very small amount of a liquid on the order of 100 $\mu$l or less is quantitatively dispensed. The liquid dispensed may be a sample or a reagent.

The mechanism for lowering the sensor to approach the surface may be installed on the support frame supporting the pipette lowering mechanism or installed on a separate support frame independently from the pipette supporting frame. It is preferred that the point at which the sensor detects the liquid surface is horizontally as close as possible to the point where the lower end of the nozzle is partially immersed in the liquid to obtain a high degree of precision in the dispensing of the liquid.

The foregoing and other objects, features and advantages of the invention will be apparent from the following more particular description of a preferred embodiment of the invention as illustrated in the accompanying drawings.

DETAILED DESCRIPTION OF THE INVENTION

Figure 1A:
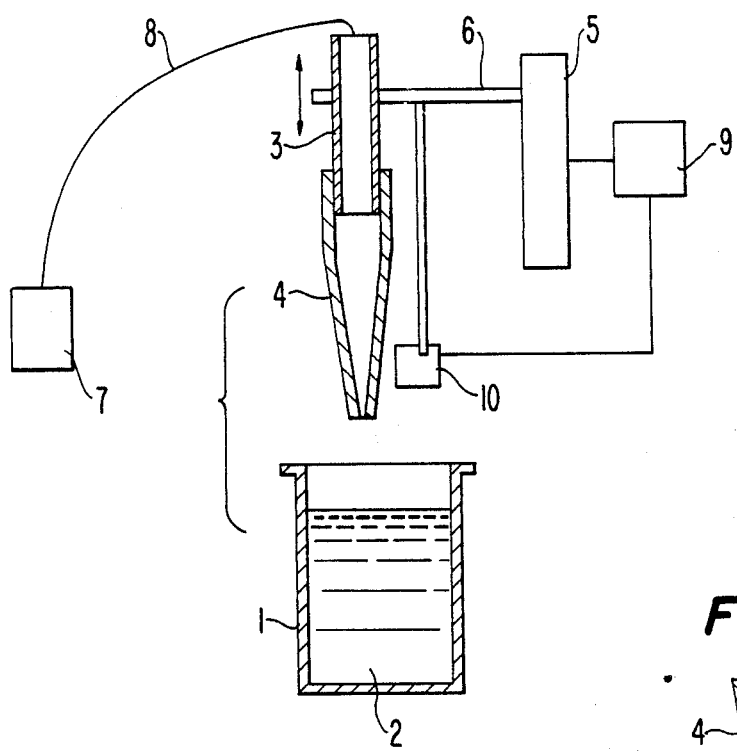
FIG. 1(a) is a schematic diagram showing a first embodiment of a quantitative liquid dispenser according to the present invention with the pipette disposed above the liquid reservoir.
Figure 1B:
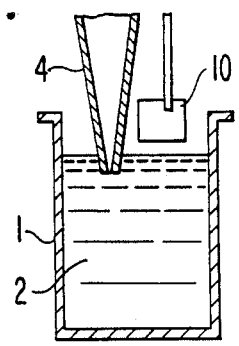
FIG. 1(b) is a partial view of the dispenser shown in FIG. 1(a) with the tip of the pipette immersed in a liquid.

The quantitative liquid dispenser as shown in FIG. 1 is comprised of a pipette 3 having a disposable tip 4 which is adapted to be moved into and out of a liquid sample contained in a sample vessel 1. The pipette 3 is carried by a supporting rod or frame 6 which in turn is moved vertically by means of a drive mechanism 5 including a pulse motor under the control of a drive control circuit 9. A spot type reflection sensor 10 is also firmly supported by the support rod or frame 6 for movement with the pipette. The sensor 10 is disposed slightly higher than the lower end of the disposable tip 4 and an electrical signal from the sensor 10 is supplied to the control circuit 9 for controlling the drive mechanism 5. When the pipette 3 is positioned over the liquid sample 2 the pipette 3 may be lowered from the position shown in FIG. 1(a) to the position shown in FIG. 1(b) wherein the lower end of the disposable tip 4 is immersed in the liquid to a degree determined by the optical sensor 10. With the lower end of the disposable tip 4 immersed in the liquid 2 as shown in FIG. 1(b) a predetermined amount of liquid is drawn up into the pipette by means of a negative pressure applied to the pipette 3 through a tube 8 under the control of a liquid volume controller 7. The pipette 3 is then raised to the position shown in FIG. 1(a) and the liquid therein may be subsequently dispensed by application of a positive air pressure through the tube 8 to the pipette 3 under the control of the liquid volume controller 7.

Figure 2A:
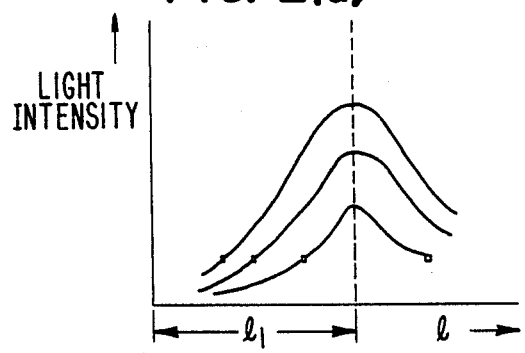
FIG. 2(a) is a graph showing light intensity curves.

The sensor 10 can be constructed using, for example an optical reflective sensor such as the HEDS-1000 (Yokokawa Hewlett Packard Corp.). Such a spot type reflection sensor 10 emits light toward the surface of the liquid 2 in the sample vessel 1 in which the lower end of the nozzle tube 4 is to be immersed and receives light reflected from the surface of the liquid. The intensity of the reflected light reaches a maximum when the sensor 10 reaches a point above the surface equal to the focal distance of the lens within the detector, the focal distance being preset by selecting an appropriate convex lens such as that shown in FIG. 4(b). The plot diagram of several light intensity curves shown in FIG. 2(a) shows the relationship of the light intensity relative to the distance 1 of the detector above the surface of the liquid. The distance $l_1$ from the surface of the liquid where the maximum intensity is obtained is constant as shown in FIG. 2(a) regardless of the reflectivity of the liquid surface or the degree of concavity or slanting of the surface. Thus the depth of immersion of the nozzle tip into the liquid can be controlled with a high degree of accuracy. The maximum intensity of the light can be detected by using a high-peak detecting circuit such as that shown in FIG. 5 so that the downward movement of the pipette is stopped when the maximum value is detected or when the pipette moves a very short distance past the point of maximum intensity.

Figure 2B:
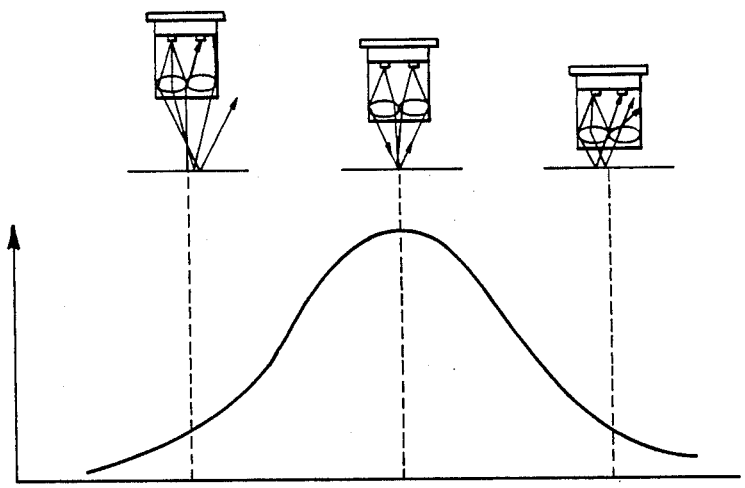
FIG. 2(b) is a schematic diagram showing the relationship of an optical sensor according to the present invention relative to various points on a light intensity curve where the liquid is level.
Figure 2C:
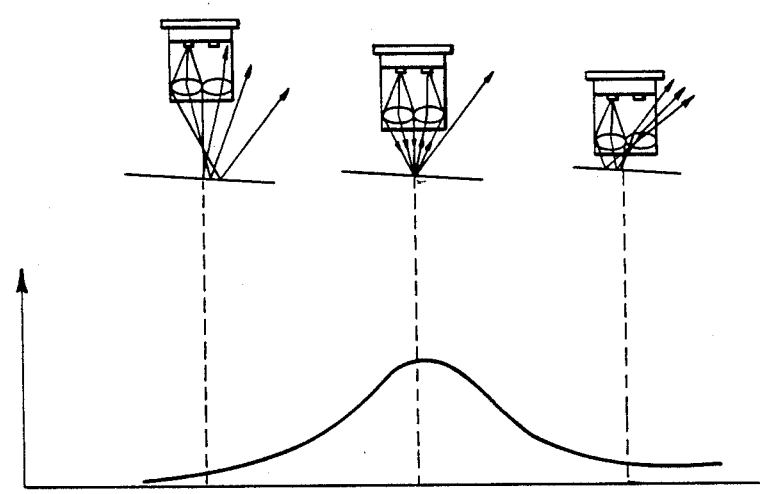
FIG. 2(c) is a view similar to FIG. 2(b) showing the relationship of the optical sensor relative to a slanted surface.

FIG. 2(b) shows three representative positions of a light detector relative to a flat liquid surface with respect to three different portions of a light intensity curve such as that shown in FIG. 2(a). The focal point of the lens in the middle position is coincident with the surface of the liquid and the light intensity is at a maximum. FIG. 2(c) shows a similar illustration but with the surface of the liquid concave or slanted. The overall intensity of the reflected light will be less in such a situation than with the flat surface as in FIG. 2(b) but the light intensity will still be at a maximum when the focal point of the lens is coincident with the surface of the liquid. When the maximum or peak value of the light intensity is expressed as 100, the light intensity detected at a 0.2 mm deviation from the focal length representing the maximum or peak value may be lowered by about ten percent.

Figure 3:
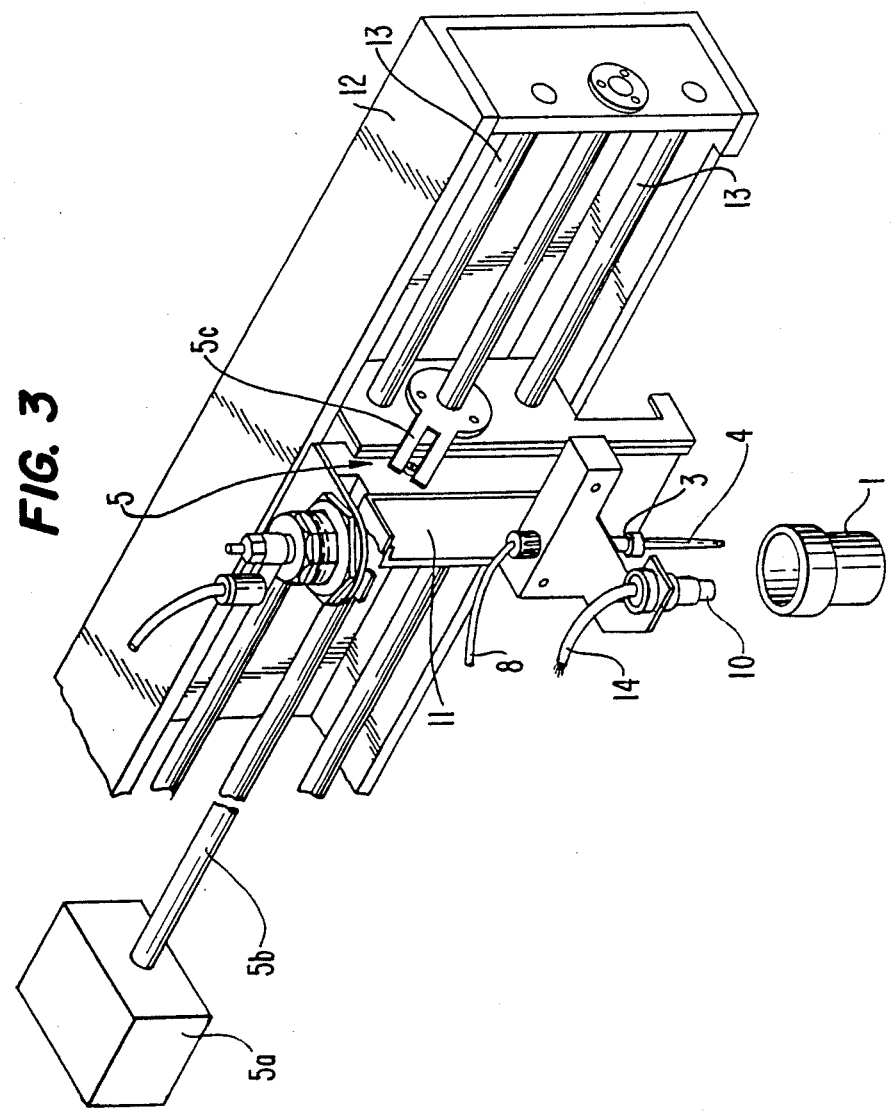
FIG. 3 is a partial perspective view of the apparatus for moveably supporting a pipette and optical sensor for movement relative to a liquid reservoir.

FIG. 3 shows one embodiment of an apparatus suitable for carrying out the present invention which corresponds to the schematic arrangement shown in FIG. 1. In FIG. 3 the numerical references 1, 3, 4, 8, and 10, represent the same elements as shown in FIG. 1. For moving the pipette up and down the rotating shaft 5b is rotated by means of a pulse motor 5a to rotate the cam 5c in an amount corresponding to the amount of rotation of the pulse motor so that the frame 11 supporting the pipette 3 is moved downwardly. In this way the disposable nozzle 4 detachably connected to the lower end of the pipette 3 moves downwardly a corresponding amount and enters the liquid within the sample vessel. The point at which the downwardly moving nozzle stops is determined by detecting the maximum value of the intensity of the reflected light by the sensor 10 which is mounted on the same support frame 11 as the pipette 3. The detector 10 is connected to the detecting circuit and a source of power by means of the cable 14. The support frame 11 is moveable horizontally along guide rods 13 carried by a main frame 12 so as to allow the pipette to be moved selectively between various vessels and reaction chambers. The support frame 11 may be moved along the guide rails 13 by any suitable means which have not been shown since such means are conventional in the art.

Figure 4A:
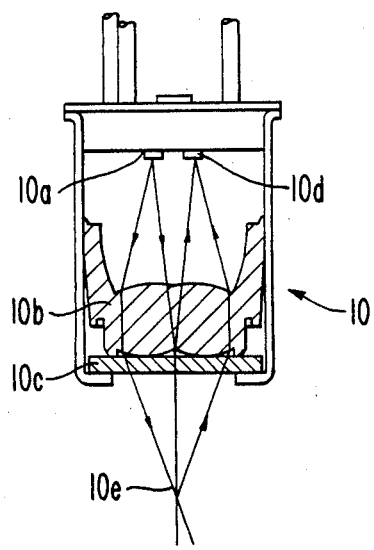
FIG. 4(a) is a detailed sectional view of an optical detector according to the present invention.
Figure 4B:
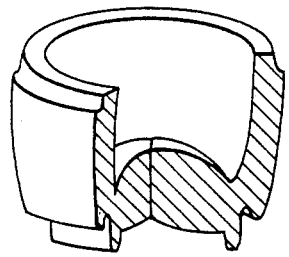
FIG. 4(b) is a slant and partially cross sectional view of the optical element in FIG. 4(a)

The photosensor 10 is shown in detail in FIG. 4 and includes an LED light source 10a and a photodiode 10d mounted in side by side relation. The light from the LED light source is projected outwardly of the glass window 10c through the convex lens 10b having its focal point at 10e. The light reflected from the liquid surface passes through the convex lens 10b and enters the photodiode 10d. The signal input and output of the sensor 10 are connected to the drive control mechanism 9 as shown in FIG. 1 through the cable 14 so that the maximum value of the intensity of the light incident on the photodiode is detected. The convex lens element shown in FIG. 4(b) is prepared by molding plastic material as one body with a skirt portion and a collar portion in such a shape as if two convex lenses are combined.

Figure 5:
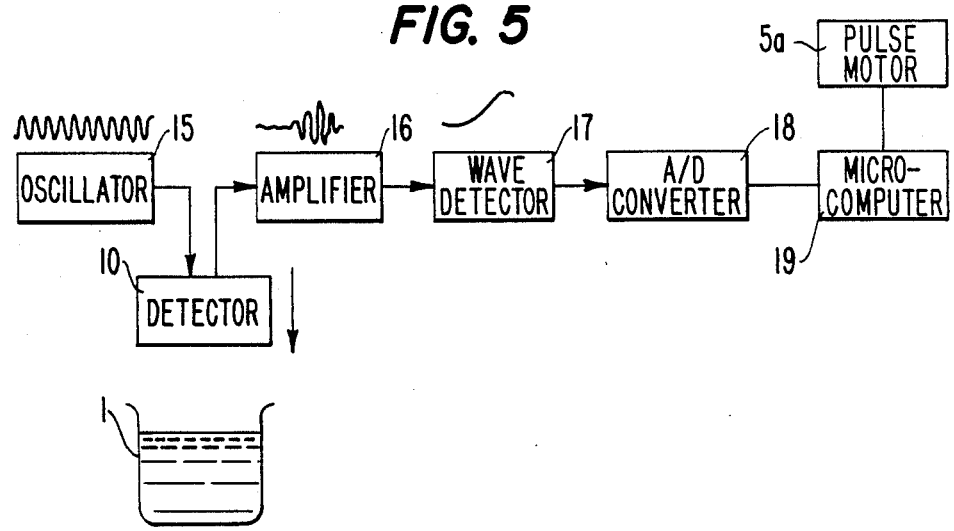
FIG. 5 is a schematic circuit diagram for detecting the maximum light intensity detected by the optical sensor.

FIG. 5 shows a block circuit diagram for the detection of the maximum intensity of the incident light in which an oscillator 15 supplies a signal to the detector 10 to activate the LED light source 10a. The signal from the photodiode 10d is passed through an amplifier 16, a wave detector 17 and an A/D converter 18 prior to being supplied to a microcomputer 19. A desired high peak detector can be constructed using the above components by a person having ordinary skill in the electrical arts. When the maximum value or peak of light intensity is detected by the microcomputer 19, such information is transmitted to the pulse motor 5a to stop the downward movement of the pipette 3.

Figure 6:
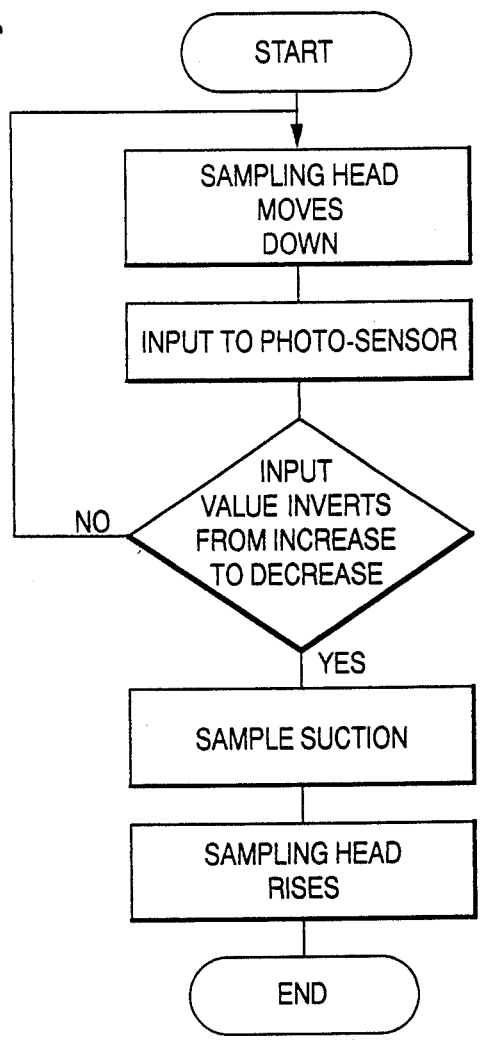
FIG. 6 is a flow chart for a process carried out with the apparatus according to the present invention.
Figure 7:
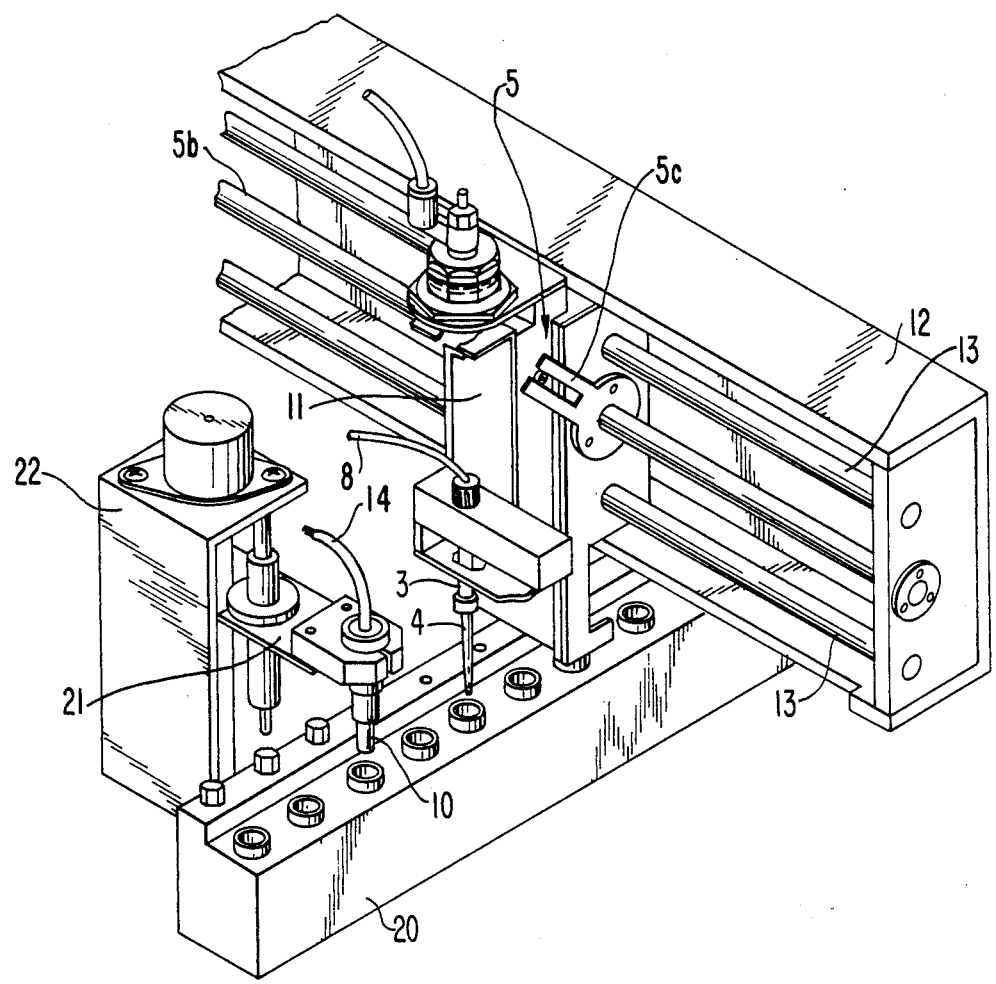
FIG. 7 is a partial perspective view of a further embodiment of the apparatus for moveably supporting a pipette and optical sensor separate from each other.
Figure 8:
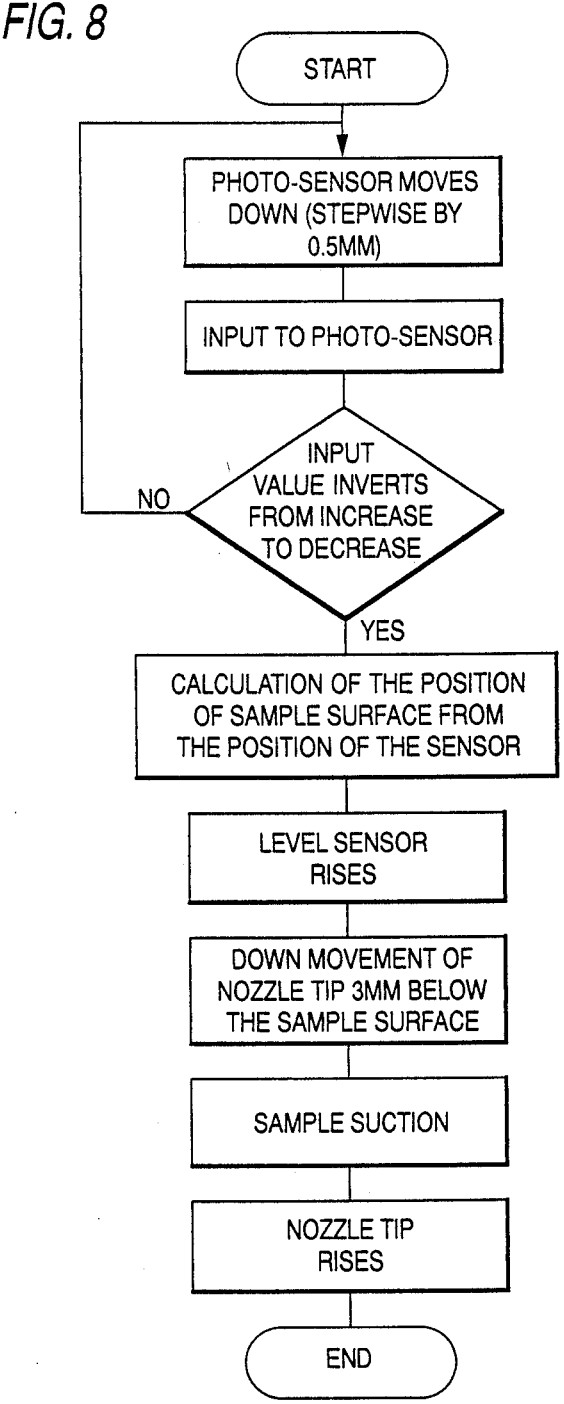
FIG. 8 is a flow chart showing the operational sequence for the apparatus shown in FIG. 7.

FIG. 6 is a flow chart showing the operational sequence for the embodiments described above. Although the support frame 11 moves horizontally as described above the operational sequence is limited to the up and down movement of the pipette which is carried by the support frame 11. At the start of operation the sampling head moves downwardly and a light signal is supplied by the photosensor as the light from the photodiode is reflected from the surface of the liquid below the sampling head. As the input value changes from an increase to decrease the downward movement of the sampling head is stopped, a sample is withdrawn from the liquid reservoir and the sampling head subsequently rises to complete the operational cycle. The focal length of the sensor 10 is 4.3 mm, and the distance from the lower end of the sensor to the lower end of the nozzle tip is 0.3 mm. In this example the nozzle and sensor were fixed to the same control mechanism as shown in FIGS. 1 and 3. FIG. 7 shows a further embodiment of the present invention wherein the pipette 3 and the sensor 10 are mounted separately from each other on separate support mechanisms. A detector 10 is carried by a supporting frame 21 which is mounted in a mechanism 22 for moving the same up and down. The pipette 3 is mounted for movement by means of a mechanism similar to that described above with respect to FIG. 3 and the details of such movement need not be repeated. As in the previous embodiment, a downward movement of the sensor is detected and when the maximum value of reflected light intensity is detected the pulse motor for moving the pipette is controlled to limit the immersion of the tip of the pipette in the liquid. In the embodiment of FIG. 7 the sample vessels are shown as being mounted in a rack 20 and suitable means may be provided for moving the pipette and detector and the rack relative to each other to align the pipette with different samples. In this embodiment for determining the position at which the downward moving nozzle is stopped, the volume of sample in one vessel is measured and memorized in a memory in the control mechanism, and then when the sample vessel comes just below the nozzle the position at which the nozzle is stopped is determined on the basis of the memorized sample volume measurement of the vessel. FIG. 8 is a flow chart showing the operational sequence of the device of FIG. 7. As an example, when the sample vessel 1 has a diameter of 11 mm and a pipette having a capacity of 200 $\mu l$ is used, a liquid volume of 5 $\mu l$ is picked up with the lower end of the nozzle tip being immersed to a depth of 3 mm below the surface of the liquid. It was noted that the dispersion with respect to the depth of immersion of the nozzle tip was 1 mm or less and with respect to the volume of liquid picked up was two percent or less.

According to the present invention the quantitative dispensing of a minute volume of liquid can be formed with an extremely high degree of precision. As a result the various quantitative and qualitative analyses can be accurately and precisely controlled. It is obvious that the device according to the present invention can be applied to a number of automatic analytical systems and analysers.

While the invention has been particularly shown and described with reference to preferred embodiments thereof it will be understood by those in the art that the foregoing and other changes in form and details may be made therein without departing from the spirit and scope of the invention.

What is claimed is:

1. A quantitative dispenser for a liquid, comprising; pipette means having a downwardly directed nozzle adapted to pick up and deliver a predetermined quantity of a liquid, drive means for moving said pipette means downwardly to immerse the lower end of said nozzle in a liquid supply, and liquid supply level sensing means for determining the stopping point for the downward movement of said pipette means, said liquid supply level sensing means being comprised of housing means, lens means mounted in said housing means and having a focal point outside of said housing means, light source means mounted in said housing means for directing a beam of light through said lens means onto the surface of said liquid supply, photosensor means mounted in said housing means for receiving light reflected from said surface of said liquid supply through said lens means, and control means operatively connected to said photosensor means and said drive means for controlling the operation of said drive means so as to stop the downward movement of said pipette means when the maximum intensity of reflected light is detected by said photosensor means, wherein said lens means comprises two convex lens portions so that said beam of light from said light source means is directed through a first one of said two convex lens portions and said light reflected from said surface passes through a second one of said two convex lens portions which has a focal point on said photosensor means whereby the maximum intensity of reflected light occurs when the surface coincides with the focal point of the first lens portion.

2. A quantitative dispenser for a liquid as set forth in claim 1, further comprising means connecting said pipette means and said detector means together for simultaneous downward movement toward said liquid supply.

3. A quantitative dispenser for a liquid as set forth in claim 1, further comprising mounting means for said detector means and means for moving said mounting means vertically independently of said means for moving said pipette means.

4. A dispenser for a liquid, comprising;
pipette means having a downwardly directed nozzle, drive means for moving said pipette means downwardly to immerse a lower end of said nozzle in a liquid supply;
liquid supply level sensing means for determining a stopping point for the downward movement of said pipette means;
said liquid supply level sensing means comprising:
housing means;
lens means mounted in said housing means and having a focal point below and outside of said housing means;
light source means mounted in said housing means for directing a beam of light through said lens means onto the surface of said liquid supply;
photosensor means mounted in said housing means for receiving light reflected from said surface of said liquid supply through said lens means; and
control means operating in response to said photosensor means for controlling the operation of said drive means so as to stop the downward movement of said pipette means when said lens means has been lowered to a position above said surface of said liquid by a distance approximately a focal length of said lens means,
wherein said lens means comprises two convex lens portions so that said beam of light from said light source means is directed through a first one of said two convex lens portions and said light reflected from said surface passes through a second one of said two convex lens portions which has a focal point on said photosensor means whereby the maximum intensity of reflected light occurs when the surface coincides with the focal point of the first lens portion.

5. A dispenser as claimed in claim 4, wherein said nozzle and said liquid supply level sensing means are arranged such that at least the lower end of said nozzle is immersed in said liquid when the lower portion of said liquid supply level sensing means is distanced above said liquid surface by approximately said focal length.

6. A dispenser as claimed in claim 4, wherein said housing means is connected to said pipette means and driven jointly with said pipette means by said drive means.

7. A dispenser as claimed in claim 4, wherein said control means comprises means for detecting the intensity of said reflected light, including circuit means for determining when said intensity reaches a maximum value, wherein said maximum intensity occurs when said lens means is positioned above the surface of said liquid by a distance equal to the focal length of said lens means.

8. A dispenser as claimed in claim 7, wherein said circuit means comprises microcomputer means.

9. A quantitative dispenser for a liquid comprising;
pipette means having a downwardly directed nozzle for immersion in a liquid sample, drive means for controlling the downward movement of said pipette means to immerse the lower end of said nozzle in said liquid; and
liquid level sensing means arranged above said lower end of said nozzle, said liquid level sensing means including a light source, lens means for projecting light from said light source onto the surface of said liquid, photosensor means for detecting light reflected from said liquid surface through said lens means, and peak detecting means for determining when the intensity of said reflected light at said photosensor means reaches a maximum value, said peak detecting means controlling said drive means so as to stop the downward movement of said pipette means and said liquid level sensing means upon detection of said maximum intensity level, wherein said lens means has a predetermined focal length,
wherein said lens means comprises two convex lens portions so that said beam of light from said light source means is directed through a first one of said two convex lens portions and said light reflected from said surface passes through a second one of said two convex lens portions which has a focal point on said photosensor means whereby the maximum intensity of reflected light occurs when the surface coincides with the focal point of the first lens portion.

10. A quantitative dispenser for a liquid, comprising;
pipette means having a downwardly directed nozzle;
drive means for moving said pipette means downwardly to immerse a lower end of said nozzle in a liquid supply;
liquid supply level sensing means for determining a stopping point for the downward movement of said pipette means;
said liquid supply level sensing means comprising;
housing means;
lens means mounted in said housing means and having a focal point below and outside of said housing means;
means for moving said lens means toward and away from the surface of said liquid supply;
light source means mounted in said housing means for directing a beam of light through said lens means onto the surface of said liquid supply;
photosensor means mounted in said housing for receiving that part of the light reflected from the surface of said liquid supply which passes through said lens means; and
control means receiving the output of said photosensor means and controlling downward movement of said lens means such that said lens means is lowered to a position above said surface of said liquid by a distance approximating a focal length of said lens means, said control means subsequently controlling the operation of said drive means so as to stop the downward movement of said pipette means at a position determined in accordance with the extent of said downward movement of said lens means,
wherein said lens means comprises two convex lens portions so that said beam of light from said light source means is directed through a first one of said two convex lens portions and said light reflected from said surface passes through a second one of said two convex lens portions, which as a focal point on said photosensor means whereby the maximum intensity of reflected light occurs when the surface coincides with the focal point of the first lens portion.

11. A dispenser as claimed in claim 10, wherein said moving means comprises second drive means, independent of said first drive means, for controlling the movement of said housing means and said lens means, the operation of said second drive means being controlled by said control means.

12. A dispenser as claimed in claim 10, wherein said control means comprises means for memorizing a value related to the extent of downward movement of said lens means, and means for controlling the downward movement of said pipette means on the basis of said memorized value.

* * * * *